United States Patent [19]

Vitands et al.

[11] Patent Number: 4,923,961
[45] Date of Patent: May 8, 1990

[54] PROCESS FOR DEODORIZING ISOBUTYLENE POLYMER

[75] Inventors: Egils Vitands, Lisle; Kelley R. Lane, Winfield, both of Ill.

[73] Assignee: Amoco Corporation, Chicago, Ill.

[21] Appl. No.: 257,513

[22] Filed: Oct. 13, 1988

[51] Int. Cl.⁵ .......................... C08F 8/04; C07C 7/12
[52] U.S. Cl. .................................. 528/482; 528/481; 528/483; 514/844; 585/255; 585/823; 585/824
[58] Field of Search .............. 528/482, 483, 490, 481; 525/333.7, 339; 424/83; 514/789, 844; 585/255, 823, 824

[56] References Cited

U.S. PATENT DOCUMENTS 4,061,780  12/1977  Yoshida et al. ................... 514/789

FOREIGN PATENT DOCUMENTS 0402243  5/1965  Japan ................................ 528/483
0124602  7/1985  Japan ................................ 528/483

Primary Examiner—Joseph L. Schofer
Assistant Examiner—F. M. Teskin
Attorney, Agent, or Firm—Matthew R. Hooper; William H. Magidson; Ralph C. Medhurst

[57] ABSTRACT

A process to hydrogenate and deodorize a polyisobutylene polymer of from 100 to 4000 molecular weight and cosmetic dermatological compositions containing the hydrogenated, deodorized polyisobutylene polymers are disclosed.

5 Claims, No Drawings

PROCESS FOR DEODORIZING ISOBUTYLENE POLYMER

FIELD OF THE INVENTION

This invention relates to hydrogenated deodorized polyisobutylenes having excellent humectant properties, a process for the preparation thereof and cosmetic formulations containing these hydrogenated deodorized polyisobutylenes. More specifically, the present invention relates to polymers of $C_4$ olefins having a viscosity of 3 to 37 centistokes at 100° F. and which are desirable as humectants in dermatological preparations for soothing dry skin conditions to improve skin protection, skin conditioning and skin therapy. These deodorized polymers of $C_4$ olefins are obtained by an improved method of preparation which results in an improved deodorized compound for use in preparations to be used on human skin.

BACKGROUND OF THE INVENTION

Deodorized polymers of $C_4$ olefins with excellent humectant properties demonstrate an improved storage and color stability at temperatures of up to 200° F. for extended periods. These polymers are prepared by polymerizing isobutylene or a mixture of $C_4$ hydrocarbon olefins containing at least two of isobutylene, 1-butene, 2-butene and butadiene in the presence of a catalyst, at a temperature within the range of from about 100° F. to about 140° F. to obtain a polyisobutylene of from about 100 to 4000 molecular weight. Another method is by stripping or by taking an overhead cut from a heavier grade of polyisobutylene to obtain a fraction of a molecular weight of from about 100 to about 4000. The polymerization product is hydrogenated and deodorized by nitrogen stripping to remove at least 2 (wt)% of the hydrogenated product and by contacting the stripped product with attapulgite clay in a ratio of 1:1 to 10:1. The deodorized $C_4$ polymers of a molecular weight range of from about 100 to about 4000 have excellent humectant properties and are desirable for use in dermatological preparations. The molecular weight range assures compatibility with many components of these preparations.

Dermatological preparations relating to treatment for irritated, pruritic and dry skin conditions have as a general objective the controlling or retarding of the degenerative or chemical breakdown of the skin sebum, lipids, protein, exudates or surface films so as to provide improved skin protection.

As a topical application, a dermatological preparation cannot have, or develop, offensive odors even though the preparation may contain perfume to add a pleasing fragrance.

Accordingly, this invention relates to deodorized substantially saturated isobutylene polymers of a molecular weight of from about 100 to about 4000, an average molecular weight of about 200 to about 350, a viscosity at 100° F. of 3-37 centistokes, color, haze—5 APHA max, haze free—10 APHA max, and bromine index—1000 max, wherein the isobutylene polymers are substantially free of odor-causing aldehydes, ketones, esters and peroxides and are suitable for replacement of squalane, fatty esters, and other moisturizing agents used in cosmetics.

Squalane, obtained from natural sources, is one of the most common moisturizer agents and is useful as a base oil for cosmetics. However, production is low, the price is high, and quality is not uniform. These problems thus make a squalane substitution desirable.

Purification of lower monoolefin polymers such as polyisobutylene has typically been by means of hydrogenation to produce a saturated compound, as is taught in U.S. Pat. No. 3,100,808 (Dyer), to render the resulting saturated polymer substantially colorless, odorless and stable. Although the hydrogenation process does reduce the odor and color-forming impurities, the hydrogenated polymer contains odor-causing aldehydes, ketones, esters and peroxides which, on storage, further oxidize to objectionable color- and odor-causing compounds.

In the prior art, U.S. Pat. No. 4,061,780 (Yoshida, et al.) teaches purification of isobutylene polymers for use in cosmetic applications wherein a liquid $C_4$ olefin fraction is polymerized in the presence of a catalyst. The polymerized reaction product is distilled to obtain a fraction having a boiling point range of 120° C. (248° F.) to 200° C. (392° F.) at 1-2 mm Hg to remove compounds having a molecular weight of less than about 250 and compounds having a molecular weight of more than 600. The resulting fraction is hydrogenated and deodorized by steam distillation under reduced pressure or treatment with activated carbon, or solvent extraction or by a combination of steam distillation, treatment with activated carbon and solvent extraction. The initial distillation of the $C_4$ polymer fraction is taught as removing compounds which can easily oxidize to form odorous compounds.

The procedure taught in the prior art to obtain a purified isobutylene polymer suitable for cosmetic use accordingly is complex, economically costly in required process equipment, and would not be easily adapted to a continuous method in a commercial application.

Accordingly, the instant invented process comprises an improved method for production of purified hydrogenated isobutylene polymer which closely matches the outstanding feel and moisturizing ability of squalane, which does not readily oxidize, contains no cyclic compounds, imparts no taste and does not deteriorate on storage. The invented process can be in batch or continuous mode, is not complex in operation and uses readily available process equipment.

SUMMARY OF THE INVENTION

The present invention is a process for the production of hydrogenated polyisobutylene polymer which is a bright, clear viscous liquid which does not readily oxidize, contains no cyclic compounds, imparts no taste, and has the feel and moisturizing ability of squalane for use in cosmetics. Hydrogenated polyisobutylene is nitrogen-stripped at a temperature of from about 290° F. to about 350° F. to remove as overhead at least 2 (wt)% to about 4 (wt)% of the charge stock. The main fraction, as the residue, is clay treated with attapulgite clay at a temperature of less than about 245° F. wherein the ratio of clay to polyisobutylene is from 1:1 to 10:1.

DETAILS OF THE INVENTION

Olefin polymers, as produced in the art from $C_4$ olefin hydrocarbons, are normally light colored and carry an oily to pungent odor associated with the refining process which produced these materials. While these attributes may not be significant in industrial applications, such characteristics render these materials unfit for more sensitive uses which require an odorless, colorless product with good stability. Hydrogenation of $C_4$ olefin polymers, such as polyisobutylene, improves the odor of the crude polymer to at least a bland odor from an odor that was more pungent, but the process of hydrogenation can cause the formation of additional odorous compounds as by-products of the process.

The deodorized polymers of $C_4$ olefins of the instant invention are prepared from a polymerized $C_4$ olefin by polymerizing isobutylene or a mixture of $C_4$ olefins at a temperature of at least 100° F., to obtain a polymer with a molecular weight range of from about 100 to about 4000. Another method to obtain a polymer of molecular weight range of about 100 to about 4000 is to strip or take an overhead cut from a heavier grade of a polyisobutylene to obtain a fraction of a molecular weight of from about 100 to about 4000. The deodorized polymers are thereupon obtained by hydrogenating the said polymer to prepare a substantially saturated hydrogenated polyisobutylene containing odorous compounds, nitrogen-stripping the hydrogenated product at a temperature of at least about 290° F. to remove a portion of the odorous compounds, and contacting the stripped product with attapulgite clay in a ratio of 1:1 to 10:1 at a temperature of less than about 245° F. to remove additional odorous compounds. The product is a purified substantially saturated isobutylene polymer of a molecular weight range of from about 100 to about 4000, of a number average molecular weight of about 200 to about 350, a viscosity at 100° F. of 3-37 centistokes, color, haze—5 APHA max, haze free—10 APHA max, bromine index—1000 max, and is substantially free of odor-causing aldehydes, ketones, esters and peroxides.

The molecular weight range of from about 100 to about 4000 advantageously provides lighter molecular weight ends to readily solubilize other compounds in formulation and a heavier molecular weight range to lend body to the final preparation when the product is used as a base oil in place of, for example, squalane, in conventional oil-based cosmetic compositions such as creams, lotions, hair oils, suntan products, baby oil, lip glosses and the like.

Hydrogenation of isobutylene polymer has been employed to prepare substantially saturated polymers (see U.S. Pat. No. 3,100,808) to reduce color, to improve product stability and to reduce the odor of the final product to a substantially odorless condition. However, despite the above improvements in product quality obtained by hydrogenation, it has been found that a detectable odor is present in a hydrogenated isobutylene polymer unless the polymer is further treated to eliminate the odor.

Steam distillation, followed by treatment with activated carbon, has been proposed to deodorize isobutylene polymers of molecular weight from 250 to 600 (see U.S. Pat. No. 4,061,780). However, it has been found that treatment with activated carbon of hydrogenated isobutylene polymers of molecular weight from 100 to about 4000 is inadequate to remove the odor-causing compounds present.

Surprisingly, it has been found that removal of the odor-causing compounds from a hydrogenated polyisobutylene polymer of from about 100 to about 4000 molecular weight can be accomplished by hydrogenation and stripping with an inert gas such as nitrogen so as to remove from about 2 wt% to about 4 wt% of the hydrogenated material in the overhead. Further treatment of the stripped product to remove other impurities and obtain a clear, haze-free product with no detectable odor by an odor panel was obtained by further treatment with attapulgite clay.

Hydrogenation of the polyisobutylene polymers can be at a temperature within the range of from about 150° F. to 700° F. with hydrogen gas at a pressure ranging from about atmospheric to about 3000 psi for a period ranging from about one minute, under strong hydrogenating conditions, up to many hours, preferably in the presence of a catalyst. Preferred hydrogenation catalysts include nickel, platinum, palladium and the like.

Hydrogenation to produce a saturated compound of the polyisobutylene, because of impurities present in the feedstock, also can result in the formation of odor and color-forming impurities considered to be aldehydes, ketones, esters and peroxides.

Hydrogenation of the polyisobutylene polymers of a molecular weight of from about 100 to about 4000, followed by nitrogen-stripping to remove 2 wt% to about 4 wt% of the charge stock and then clay percolation using attapulgite clay, produces a deodorized polyisobutylene cosmetic oil having excellent humectant properties, of a viscosity of 3 to 37 centistokes at 100° F., color, haze—5 APHA maximum, haze-free—10 APHA maximum and bromine index—1000 maximum.

The odorous compounds contained in the fraction removed by nitrogen stripping could not be isolated by liquid chromatography techniques, nor has any instrumental technique been able to accurately detect the odorous compounds. Therefore, an odor panel was used to detect the presence or absence of odor in the finished product.

Stripping less than 2 wt% has been found to be ineffective in significantly reducing the level of odorous compounds present in the hydrogenated polyisobutylene. Stripping more than 4 wt% has been found to be without value and uneconomical although an odorless product is obtained.

Attapulgite clay of from about 4 to about 200 mesh (Engelhard Corp., Edison, NJ) can be used. Preferably, attapulgite clay of 30–60 mesh is used.

The final product, the cosmetic base oil of this invention, is a bright, clear, odorless viscous liquid which is stable for long periods of time, not demonstrating any degradation due to oxidation over storage periods of up to one year under ambient temperature conditions, contains no cyclic compounds, is miscible with mineral oils and organic solvents, matches the feel and moisturizing ability of squalane, is hydrophobic but is easily emulsified. An accelerated heat treatment test can cause some color development.

This cosmetic base oil can be used in amounts of up to 50 wt% or higher in cosmetic formulations requiring an oil-base composition in accordance with conventional practice. For example, baby oil can contain almost 100 wt%.

In summary, the instant invented process comprises a method for deodorizing an odorous isobutylene polymer, hereinafter alternatively designated "polyisobutylene," of molecular weight of from about 100 to about 4000 which comprises (a) hydrogenating the polymer at a temperature of from about 300° F. to about 465° F. in the presence of a catalyst to prepare a substantially saturated hydrogenated polyisobutylene containing odorous compounds; (b) nitrogen-stripping the hydrogenated polyisobutylene to strip off from about 2 wt% to about 4 wt% of the polymer and remove a portion of the said odorous compounds and (c) percolating the nitrogen-stripped hydrogenated polyisobutylene polymer through attapulgite clay wherein the ratio of said polyisobutylene to said clay is in the range of from 10:1 to 1:1 at a temperature within the range of from about 70° F. to about 200° F., to remove additional odorous compounds, and (d) recovering the nitrogen-stripped, clay-percolated hydrogenated isobutylene polymer substantially free of impurities and odorous compounds, having a viscosity of 3 to 37 centistokes at 100° F., color, haze—5 APHA maximum, haze-free—10 APHA maximum and of a molecular weight range of from about 100 to about 4000. In more detail, the nitrogen stripping can strip, preferably, from 3 wt% to about 4 wt% of the hydrogenated polyisobutylene. The attapulgite clay is preferably 30-60 mesh. The ratio of nitrogen-stripped polyisobutylene to attapulgite clay preferably is about 10:1. The process can be a continuous process.

The instant invention comprises an oil-base cosmetic composition comprising a hydrogenated deodorized isobutylene polymer of molecular weight of from about 100 to about 4000 and conventional cosmetic ingredients for oil-based cosmetic dermatological preparations, said hydrogenated deodorized isobutylene polymer being prepared by (a) hydrogenating an isobutylene polymer of molecular weight of from about 100 to about 4000 at a temperature of from about 300° F. to about 465° F. in the presence of a catalyst to prepare a substantially saturated hydrogenated polyisobutylene containing odorous compounds; (b) nitrogen-stripping the hydrogenated polyisobutylene to strip off from about 2 wt% to about 4 wt% of the hydrogenated polyisobutylene polymer and to remove a portion of the said odorous compounds; (c) percolating the nitrogen-stripped hydrogenated polyisobutylene polymer through attapulgite clay of from 4 to about 200 mesh, wherein the ratio of said polyisobutylene to said clay is in the ratio of from 10:1 to 1:1 at a temperature within the range of from about 70° F. to about 200° F., to remove additional odorous compounds, and (d) recovering a nitrogen-stripped clay-percolated hydrogenated isobutylene polymer substantially free of impurities and odorous compounds, having a viscosity of 3 to 37 centistokes at 100° F., color, haze—5 APHA maximum, haze-free—10 APHA maximum and a molecular weight range of from about 100 to about 4000.

The following examples illustrate the process and composition of the instant invention but are not construed as limiting the scope of the invention.

EXAMPLE I

The following illustrates the method of hydrogenating isobutylene polymers of molecular weight of from about 100 to about 4000.

The equipment used was a 1000 gallon nickel reactor equipped with a radial turbine mixer, three anti-rotation baffles and a 4 foot square sparge ring. The reactor was thoroughly cleaned with water and dried with nitrogen and heat. About 5000 pounds of isobutylene polymers of molecular weight of from about 100 to about 4000 and 25 pounds of 5% palladium on active carbon powder catalyst were placed in the reactor. The reactor, with stirring, was heated to about 340° F. with steam in the reactor jacket. The reactor was then pressurized with hydrogen to 350 psig. The temperature of the reactor contents continued to rise because of the heat generated by the hydrogenation reaction. Maximum temperature reached was about 470° F. The hydrogenation reaction was essentially complete after 6 hours.

The reactor contents were then pumped through a filter precoated with celite. The final product had the following properties: viscosity - 30.4 cSt (100° F.), flash point COC—280° F., color (APHA)—0.0, haze (APHA) 0.3, bromine index 387 (0.8% unsaturation).

EXAMPLE II

The following illustrates the nitrogen stripping and clay treatment of a hydrogenated isobutylene polymer of molecular weight of from about 100 to about 4000.

A three-neck round-bottom 500 ml flask equipped with electric mantle, mechanical stirrer, thermowell and condensers was charged with 200 grams of hydrogenated polyisobutylene polymer, molecular weight of from about 100 to about 4000. Temperature of the polymer was 302° F. Nitrogen gas at 2 scfh was bubbled through the polymer for a period of one hour. Distillate was collected in a 500 ml flask.

An infrared analysis of the distillate, 3.58%, indicated presence of hydroxyl groups and carbonyl groups but the odorous compounds could not be detected by chromatography analysis.

After cooling, the stripped material was submitted to an odor panel to detect any odor. A slight odor was detectable.

The stripped material was cooled to a temperature less than 150° F. and percolated through a bed of attapulgite clay of 30-60 mesh. Ratio of polymer to clay was 10:1. The clay-treated material was clear and haze-free. No odor was detectable by an odor panel.

EXAMPLE III

Hydrogenated isobutylene polymer of molecular weight of about 100 to about 4000, as prepared in Example I, was treated with activated charcoal to remove odor. Treatment with activated charcoal was ineffective in removing odor to an acceptable level. A nitrogen-stripped clay-treated sample prepared according to the procedure of Example II was the control. Details of the activated charcoal treatments are as follows:

(A) Hydrogenated isobutylene polymer of molecular weight of from about 100 to about 4000, 500 grams, was filtered in a single pass through 25 grams of Darco-60 activated charcoal in a 2 inch glass column maintained at room temperature. The filtered product had a persistent, detectable odor by an odor panel, as compared with the control sample and had a dark color.

(B) The procedure of charcoal treatment (A) was repeated but the filtration was maintained at a temperature of 200° F. The filtered product had a persistent, detectable odor by an odor panel, as compared with the control sample, and had a dark color.

(C) Hydrogenated isobutylene polymer of molecular weight range of from about 100 to about 4000, 400 grams, and 25 grams of Darco C-60 activated charcoal were added to a suitable vessel equipped with stirring means to prepare a slurry. The mixture was slurried for one hour at room temperature with stirring and then the carbon was removed by filtration. The filtered product had a persistent, detectable odor by an odor panel, as compared with the control sample.

(D) The procedure of charcoal treatment (C) was repeated at a temperature of 302-338° F. The carbon was removed by filtration. The filtered product had a persistent, detectable odor by an odor panel, as compared with the control sample.

The above illustrates that use of activated charcoal alone is ineffective to remove a persistent, detectable odor from hydrogenated isobutylene polymer of molecular weight of about 100 to about 4000.

EXAMPLE IV

Hydrogenated isobutylene polymer of molecular weight of about 100 to about 4000, as prepared in Example I, was nitrogen stripped to remove odor in the following example. The polymer had not been charcoal treated prior to stripping. Details are as follows:

Hydrogenated isobutylene polymer of molecular weight of from about 100 to about 4000, 200 grams, was placed in a suitable vessel and nitrogen stripped at an $N_2$ flow rate of 2 scfh and a temperature of 302° F. for one hour. The overhead, condensed and weighed, was 3.5 wt% of the original charge of isobutylene polymer.

The stripped product had a persistent, detectable odor by an odor panel, as compared with a control sample prepared according to the procedure of Example II.

The above illustrates that nitrogen stripping alone, to remove 3.5 wt%, of the hydrogenated polymer is ineffective to remove a persistent, detectable odor from hydrogenated isobutylene polymer of molecular weight of from about 100 to about 4000.

EXAMPLE V

Hydrogenated isobutylene polymer of molecular weight of about 100 to about 4000, as prepared in Example II, was treated with attapulgite clay to remove odor. Treatment with attapulgite clay was ineffective in removing color to an acceptable level. A nitrogen-stripped clay-treated sample prepared according to the procedure of Example II was the control. Details of the clay treatment are as follows:

(A) Hydrogenated isobutylene polymer of molecular weight of from about 100 to about 4000, 800 cc, was filtered in a single pass through 40 ml of attapulgite clay, 30-60 mesh, in a 250 ml buret maintained at room temperature. The filtered sample had a persistent detectable odor, as compared with the control sample, by an odor panel.

(B) The procedure of clay treatment (A) was repeated using a glass funnel equipped with a funnel heating mantle. The filtration was maintained at a temperature of 150° F. The filtered product had a persistent, detectable odor by an odor panel, as compared with the control sample.

(C) The procedure of clay treatment (B) was repeated at a temperature of 200° F. The filtered product had a persistent, detectable odor by an odor panel, as compared with the control sample.

(D) The procedure of clay treatment (B) was repeated at a temperature of 250° F. The filtered product had a persistent, detectable odor by an odor panel, as compared with the control sample.

The above illustrates that clay treatment alone is ineffective to remove a persistent, detectable odor from hydrogenated isobutylene polymer of from about 100 to about 4000 molecular weight.

EXAMPLE VI

Hydrogenated isobutylene polymer of molecular weight of from about 100 to about 4000 which was nitrogen stripped and clay treated, as prepared in Example II, was heat-treated for a period of 28 days. Heat aging was performed by placing 65 ml of product into color measurement tubes. The tubes were then placed in a Hot Pack electric heat oven for the specified times. Samples were cooled before colors were measured. The samples were kept at temperatures of 140° F. and 200° F. APHA color and haze measurements were made at intervals of 7 days. An odor panel also monitored the samples. Details are as follows:

| Effect of Heat Aging On Deodorized Hydrogenated Polyisobutylene | | | |
|---|---|---|---|
| Sample Temperature | No. Days | APHA Color* Haze | Haze-Free** |
| 140° F. | 0 | 0 | 0 |
| 200° F. | 0 | 0 | 0 |
| 140° F. | 7 | 0 | 0 |
| 200° F. | 7 | 0 | 0 |
| 140° F. | 14 | 0 | 0 |
| 200° F. | 14 | 0 | 20 |
| 140° F. | 21 | 0 | 0 |
| 200° F. | 21 | 0 | 40.4 |
| 140° F. | 28 | 0 | 0 |
| 200° F. | 28 | 0 | 53.8 |

*APHA color-measured by a spectrographic method which has been correlated to standard APHA color as described by ASTM Method D-1209.
**Haze-free-measured by the same spectrographic measurement as above except the absorbence due to the haze has been subtracted before the calculation has been made to determine APHA color.

The odor panel detected no increase in odor in either the 140° F. or 200° F. sample.

The above heat treating test indicates that hydrogenated polyisobutylene polymers of molecular weight range of from about 100 to about 4000, as prepared in Example II, are stable as to haze and odor at elevated temperatures. A slight increase in color can be detected if the polymer is kept at an elevated temperature for an extended period.

EXAMPLE VII

The hydrogenated isobutylene polymers of molecular weight of about 100 to about 4000 hydrogenated and deodorized by the process of the instant invention and other ingredients were mixed to prepare a sunscreen cream.

| | wt % |
|---|---|
| Hydrogenated Polyisobutene | 5.0 |
| Glyceryl Stearate | 6.0 |
| Cetearyl Alcohol | 1.0 |
| Cetearyl Octanoate | 6.0 |
| Triethanolamine | 1.5 |
| Cetearyl Octanate | 2.0 |
| Propylene Glycol | 2.0 |
| Benzophenone-3 | 3.0 |
| Stearyl Alcohol | 2.0 |
| Benzophenone-4 | 3.0 |
| Water, perfume, preservative | Balance |

The product is a smooth, glossy cream with substantial UVB protection.

EXAMPLE VIII

The hydrogenated isobutylene polymers of molecular weight of about 100 to about 4000 purified and deodorized by the process of the instant invention were mixed with other ingredients to prepare a hand cream.

| | wt % |
|---|---|
| Glyceryl Monostearate (S.E.) | 4.0 |
| Stearic Acid TP | 4.0 |
| Cetyl Alcohol | 2.0 |

-continued

| | wt % |
|---|---|
| Lanolin | 2.0 |
| Hydrogenated Polyisobutylene | 4.0 |
| Propylene Glycol | 3.0 |
| Triethanolomine | 1.0 |
| Preservative | 0.2 |
| Water and Perfume | Balance |

The product is a hand cream with desirable humectant properties that is a smoothing, dry skin conditioning dermatological preparation.

What is claimed is:

1. A process for deodorizing an odorous isobutylene polymer of molecular weight of from about 100 to 4000 for cosmetic applications, which process comprises:
    (a) hydrogenating said polymer at a temperature of about 300° F. to about 465° F. in the presence of a catalyst, to prepare a substantially saturated hydrogenated isobutylene polymer containing odorous compounds,
    (b) nitrogen-stripping said hydrogenated isobutylene polymer at a temperature within the range of from about 290° F. to about 350° F. for a period sufficient to strip off from about 2 wt% to about 4 wt% of said hydrogenated isobutylene polymer to remove a portion of said odorous compounds, and to prepare a nitrogen-stripped hydrogenated isobutylene polymer,
    (c) percolating said nitrogen-stripped hydrogenated isobutylene polymer through attapulgite clay of from about 4 to about 200 mesh wherein the ratio of said isobutylene polymer to said clay is in the range of from 10:1 to 1:1 at a temperature within the range of from about 70° F. to about 200° F. to remove additional odorous compounds, and
    (d) recovering the nitrogen-stripped, clay-percolated hydrogenated isobutylene polymer substantially free of impurities and odorous compounds, being colorless and odorless, having a viscosity of 3 to 37 centistokes at 100° F., color, haze—5 maximum, haze-free—10 APHA maximum, and of a molecular weight range of from about 100 to about 4000.

2. The process of claim 1 wherein from about 3 wt% to about 4 wt% of said hydrogenated isobutylene polymer is stripped from said hydrogenated isobutylene polymer by said nitrogen stripping.

3. The process of claim 1 wherein ratio of nitrogen-stripped isobutylene polymer to attapulgite clay is 10:1.

4. The process of claim 1 wherein said attapulgite clay is 30–60 mesh.

5. The process of claim 1 wherein the process is a continuous process.

* * * * *